United States Patent
Thiebaut

(10) Patent No.: US 7,498,016 B2
(45) Date of Patent: Mar. 3, 2009

(54) PREPARATION OF SYNGAS FOR ACETIC ACID SYNTHESIS BY PARTIAL OXIDATION OF METHANOL FEEDSTOCK

(75) Inventor: Daniel Marcel Thiebaut, Lescar (FR)

(73) Assignee: Acetex (Cyprus) Limited, Limassol (CY)

(*) Notice: Subject to any disclaimer, the term of this patent is extended or adjusted under 35 U.S.C. 154(b) by 0 days.

(21) Appl. No.: 11/569,592

(22) PCT Filed: Jun. 23, 2005

(86) PCT No.: PCT/CY2005/000001

§ 371 (c)(1),
(2), (4) Date: Nov. 25, 2006

(87) PCT Pub. No.: WO2006/005269

PCT Pub. Date: Jan. 19, 2006

(65) Prior Publication Data

US 2007/0225384 A1 Sep. 27, 2007

Related U.S. Application Data

(60) Provisional application No. 60/586,547, filed on Jul. 9, 2004.

(51) Int. Cl.
 C01B 3/24 (2006.01)
 C01B 31/18 (2006.01)
 C07C 27/00 (2006.01)

(52) U.S. Cl. .................. 423/650; 423/418.2; 518/700; 518/702; 518/703; 518/704

(58) Field of Classification Search .............. 518/700, 518/702, 703, 704; 423/418.2, 650
See application file for complete search history.

(56) References Cited

U.S. PATENT DOCUMENTS 4,110,359 A * 8/1978 Marion .............. 518/703
2002/0085963 A1* 7/2002 Vidalin .............. 422/187

* cited by examiner

Primary Examiner—Jafar Parsa
(74) Attorney, Agent, or Firm—Daniel N. Lundeen; Lundeen & Lundeen, PLLC

(57) ABSTRACT

A method for the production of syngas from methanol feedstock is disclosed. The methanol feed (110) is supplied to a partial oxidation reactor (112) with oxygen (114) and optionally steam (116) to yield a mixed stream (118) of hydrogen, carbon monoxide, and carbon dioxide. The carbon dioxide (122) is separated out and the hydrogen and carbon monoxide mixture (124) is fed to a cold box (126) where it is separated into hydrogen-rich and carbon monoxide-rich streams (130, 128). The separated carbon dioxide (122) can be recycled back to the partial oxidation reactor (112) as a temperature moderator if desired. The carbon monoxide-rich stream (128) can be reacted with methanol (134) in an acetic acid synthesis unit (132) by a conventional process to produce acetic acid (136) or an acetic acid precursor. Optionally, an ammonia synthesis unit (144) and/or vinyl acetate monomer synthesis unit (156) can be integrated into the plant.

18 Claims, 10 Drawing Sheets

PREPARATION OF SYNGAS FOR ACETIC ACID SYNTHESIS BY PARTIAL OXIDATION OF METHANOL FEEDSTOCK

BACKGROUND OF THE INVENTION

This invention generally relates to a method for the process for making hydrogen and carbon monoxide by partial oxidation reforming of a lower alcohol, e.g., methanol, and more particularly to a process for making acetic acid from a methanol feedstock and carbon monoxide obtained by partial oxidation of methanol.

In recent years, methanol production has increased in countries with high gas production due the development of high capacity plants utilizing high yield processes, for example, the Mega-methanol technology. Market conditions in different locations can often result in relatively low methanol prices (in the case of an oversupply) and relatively high natural gas prices (in the case of a shortage), due generally to excessive usage in the heating of buildings and homes, and as well as high usage in power plants. For example, in chemical plants where syngas is produced for the purpose of extracting CO for the synthesis of acetic acid, high costs can make natural gas cost prohibitive as a feedstock.

The primary raw materials in acetic acid manufacture are carbon monoxide (CO) and methanol. By retrofitting existing methanol plants to include acetic acid synthesis units, it is possible to eliminate the step of importing methanol for the synthesis of acetic acid, instead producing methanol in situ for the acetic acid synthesis. The retrofit of existing methanol plants for the manufacture of acetic acid is known in the art. Representative references disclosing this and similar processes include U.S. Pat. No. 6,232,352 to Vidalin, U.S. Pat. No. 6,274,096 to Thiebaut et al, and U.S. Pat. No. 6,353,133 to Thiebaut et al, each of which is hereby incorporated by reference.

In U.S. Pat. No. 3,920,717, Marion discloses a continuous process for the production of methanol from solid and/or liquid hydrocarbon material in a catalyst free reaction zone using a partial oxidation reactor. In U.S. Pat. No. 4,006,099, Marion et al. disclose improved combustion efficiency in the non-catalytic partial oxidation of liquid hydrocarbonaceous materials in a double-annulus-type burner. In U.S. Pat. Nos. 4,081,253 and 4,110,359, Marion discloses a method for producing synthesis gas, substantially comprising H2 and CO and having a mole ratio (H2/CO) of about 0.5 to 1.9 by partial oxidation of a hydrocarbonaceous fuel with substantially pure oxygen.

The use of partial oxidation reactors for the reforming of natural gas feedstock to syngas is well known in the art. Representative references disclosing partial oxidation reactors for the production of syngas include U.S. Pat. No. 2,896,927 to Nagle et al; U.S. Pat. No. 3,920,717 to Marion; U.S. Pat. No. 3,929,429 to Crouch; and U.S. Pat. No. 4,081,253 to Marion, each of which is hereby incorporated herein by reference.

The manufacture of hydrogen from methanol using a methanol reforming catalyst alone or in conjunction with a hydrogen-generating shift reactor is known in the art. Representative references disclosing this and similar processes include U.S. Pat. No. 4,175,115 to Ball et al; U.S. Pat. No. 4,316,880 to Jockel et al; U.S. Pat. No. 4,780,300 to Yokoyama; and U.S. Pat. No. 6,171,574 to Juda, each of which is hereby incorporated herein by reference.

The manufacture of acetic acid from carbon monoxide and methanol using a carbonylation catalyst is well known in the art, as demonstrated by representative references disclosing this and other similar processes including U.S. Pat. No. 1,961,736 to Carlin et al; U.S. Pat. No. 3,769,329 to Paulik et al; U.S. Pat. No. 5,155,261 to Marston et al; U.S. Pat. No. 5,672,743 to Garland et al; U.S. Pat. No. 5,728,871 to Joensen et al; U.S. Pat. No. 5,817,869 to Hinnenkamp et al; U.S. Pat. Nos. 5,877,347 and 5,877,348 to Ditzel et al; U.S. Pat. No. 5,883,289 to Denis et al; and U.S. Pat. No. 5,883,295 to Sunley et al, each of which is hereby incorporated by reference herein.

The primary raw materials for vinyl acetate monomer (VAM) manufacture are ethylene, acetic acid and oxygen. Carbon dioxide is produced as an undesirable byproduct in the reaction and must be removed from the recycled ethylene. A significant expense of new production capacity for syngas, methanol, acetic acid and acetic acid derivatives such as VAM, is the capital cost of the necessary equipment. Other significant expenses include the operating costs, including the cost of raw materials. It would be desirable if these capital and operating costs could be reduced.

As far as applicant is aware, there is no disclosure in the prior art for supplying a methanol feedstock to a partial oxidation reactor to produce hydrogen and carbon monoxide for the synthesis of acetic acid. Further, as far as applicant is aware, there is no disclosure in the prior art for modifying existing methanol plants having partial oxidation reactors to reform a lower alcohol, e.g. methanol, in the presence of carbon dioxide, oxygen, steam or a combination thereof.

SUMMARY OF THE INVENTION

The present invention is directed to a method for the preparation of syngas from the partial oxidation of methanol for use when the costs of methanol feedstock are low relative to the costs of natural gas, and more particularly to a method for the preparation of acetic acid from methanol and CO, where the CO is separated from syngas produced by the partial oxidation of a methanol feedstock.

The present invention provides, in one embodiment, a method for preparing a hydrogen-rich stream and a carbon monoxide-rich stream. The method includes the steps of (a) reacting a methanol feed stream and an oxygen rich stream, and optionally a temperature moderator, in a partial oxidation reactor to produce a syngas stream, (b) separating the syngas stream into a carbon dioxide rich stream and a mixed stream containing hydrogen/carbon monoxide, and (c) separating the mixed stream into a hydrogen-rich stream and a carbon monoxide-rich stream. The method can further include the step of vaporizing the methanol feed stream before supplying to the partial oxidation reactor. The temperature moderator can be selected from steam, carbon dioxide, nitrogen, cooled and recycled effluent, or mixtures thereof. The temperature moderator can be a carbon dioxide-rich stream recycled from the reactor effluent. The partial oxidation reactor can be catalyst-free and operated at a temperature between 1100° and 2000° C. Preferably, the partial oxidation reactor can be operated at a temperature between 1300° and 1500° C. The method can further include reacting a portion of the methanol feed stream with the carbon monoxide rich stream to produce acetic acid. The method can further include the steps of providing a nitrogen stream from an air separation unit, and supplying the nitrogen stream and the hydrogen-rich stream to an ammonia synthesis unit to produce ammonia. The method can further include the steps of providing an ethylene stream, and supplying the ethylene stream, oxygen, and acetic acid to a vinyl acetate monomer synthesis unit to produce vinyl acetate monomer. The oxygen supplied to the partial oxidation reactor and to the vinyl acetate monomer synthesis unit can be provided by a single air separation unit.

The present invention provides, in another embodiment, a method for converting an original methanol plant to a converted plant for the synthesis of acetic acid. The method includes the steps of (a) providing the original methanol plant having at least one partial oxidation reactor for converting a hydrocarbon to a syngas stream containing hydrogen, carbon monoxide and carbon dioxide; and a methanol synthesis loop for converting hydrogen and carbon monoxide from the syngas stream to methanol, (b) providing for supplying at least a portion of a methanol feedstock stream, oxygen from an air separation unit and optionally, a temperature moderator, to the at least one partial oxidation reactor, (c) installing a first separation unit for separating a carbon dioxide-rich stream and a mixed hydrogen/carbon monoxide stream from the syngas effluent, (d) installing a second separation unit for separating a hydrogen-rich stream and a carbon monoxide rich stream from the mixed stream, (e) installing an acetic acid synthesis unit, (f) providing for supplying the carbon monoxide-rich stream from the second separation unit and a portion of the methanol feedstock stream to the acetic acid synthesis unit; and (g) installing isolation valves for isolating the methanol synthesis loop from the remainder of the converted plant. The methanol feedstock can be vaporized prior to being supplied to the partial oxidation reactor. The method can further include the steps of (h) installing an ammonia synthesis unit for reacting a hydrogen-rich stream and nitrogen to form ammonia, (i) providing for supplying at least a portion of the hydrogen-rich stream from the separation unit to the ammonia synthesis unit; and (j) providing a nitrogen stream from the air separation unit to the ammonia synthesis unit. The method can further include the steps of installing a vinyl acetate monomer synthesis unit for reacting ethylene, oxygen, and acetic acid to form vinyl acetate monomer, providing for supplying at least a portion of the oxygen from an air separation unit to the vinyl acetate monomer synthesis unit; and producing a carbon dioxide-rich stream in the vinyl acetate monomer synthesis unit. The method can further include recycling the carbon dioxide-rich stream to the partial oxidation reactor.

In another embodiment, the present invention provides a method for preparing hydrogen, carbon monoxide and acetic acid from methanol. The method includes the steps of (a) supplying a vaporized methanol feed stream, an oxygen-rich stream, and optionally, a temperature moderator, to a catalyst-free partial oxidation reactor to form a syngas stream comprising hydrogen, carbon monoxide and carbon dioxide, (b) separating a carbon dioxide-rich stream and a mixed hydrogen/carbon monoxide stream from the syngas stream, (c) separating a hydrogen-rich stream and a carbon monoxide-rich stream from the mixed stream, and (d) reacting the carbon monoxide-rich stream with methanol in an acetic acid synthesis unit to produce acetic acid. The method can further include the step of recycling at least a portion of the carbon dioxide-rich stream to the catalyst free partial oxidation reactor as a temperature moderator.

DESCRIPTION OF THE INVENTION

Detailed embodiments of the present invention are disclosed herein. However, it is understood that the disclosed embodiments are merely exemplary of the invention, which can be embodied in various forms. Specific structural and functional details disclosed herein are not intended to be limiting, but merely illustrations that can be modified within the scope of the attached claims.

The plant for the process of reforming methanol in a partial oxidation reactor to produce syngas can be a new plant, or it is preferably the retrofit of an existing methanol plant which includes at least one partial oxidation reactor.

The present invention provides a solution to the problems associated with the production of syngas from natural gas when the costs of natural gas are high. When such economic conditions exist, plants designed for methanol and acetic acid synthesis can be reconfigured for the production of acetic acid using existing methanol stock as feed to the reactor, instead of natural gas.

The conversion of methanol to carbon monoxide and hydrogen is shown generally by the following reactions:

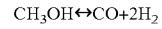

$$CH_3OH \leftrightarrow CO + 2H_2$$

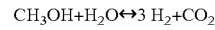

$$CH_3OH + H_2O \leftrightarrow 3H_2 + CO_2$$

If desired, carbon monoxide production can be increased via the reverse shift reaction (shown below) where carbon dioxide and hydrogen combine to form carbon monoxide and water.

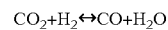

$$CO_2 + H_2 \leftrightarrow CO + H_2O$$

Figure 1:
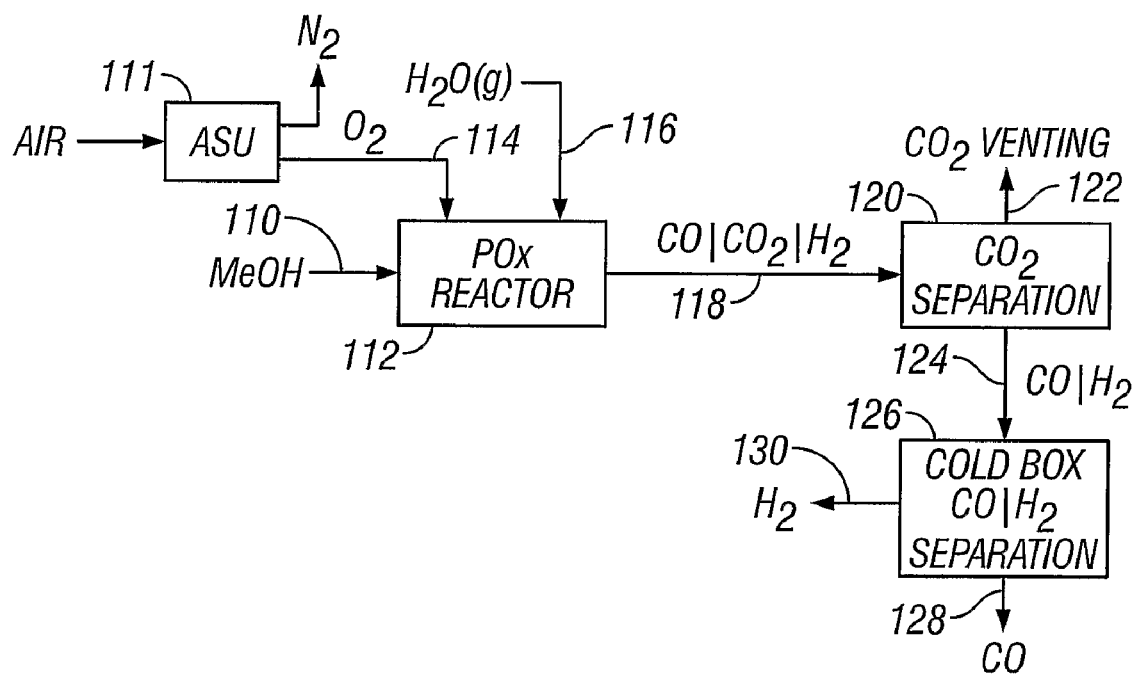
FIG. 1 is a simplified overall block flow diagram of one embodiment of the present invention for the production of hydrogen and carbon monoxide from methanol.

Referring to FIG. 1, a process is provided for the partial oxidation of a methanol feedstock stream to produce a syngas stream which can be separated into hydrogen (H2) and carbon monoxide (CO) streams for further use. A methanol stream 110 is supplied to a catalyst-free partial oxidation (POX) reactor 112 of an existing methanol synthesis plant, where it is combined with oxygen 114 and optionally steam 116. The methanol stream 110 is preferably a pre-existing purified feedstock or a commercial methanol product which has been purified by distillation or another conventional process. The oxygen 114 is obtained from an air separation unit (ASU)

111, which is supplied with compressed air. Steam 116 can preferably be provided by pre-existing facilities. Nitrogen and excess oxygen (not shown) provided by ASU 111 can be provided to controls.

If oxygen feedstock 114 is not limited, the methanol feedstock 110 can be supplied to the reactor at room temperature. If supplies of oxygen 114 are limited, however, the methanol feedstock 110 can be preheated and/or vaporized (not shown) prior to supplying to the POX reactor 112. When room temperature methanol 110 is supplied to the partial oxidation reactor 112 with an excess of oxygen 114, hydrogen content in the syngas effluent 118 is reduced.

POX reactor 112 can produce a syngas effluent 118 consisting of H2, CO and CO2. The effluent 118 is generally cleaner than syngas produced from a natural gas feed as much of the impurities were removed during synthesis of the methanol feed stream 110. Effluent 118, after cooling, can be fed to CO2 separation unit 120 which produces a CO2-rich stream 122 and a mixed CO/H2 stream 124 essentially free of CO2. The CO2-rich stream 122 can be vented and the mixed CO/H2 stream 124 can be supplied to separation unit 126.

Separation unit 126 preferably includes molecular sieves and a conventional cold box. The separation unit 126 splits the mixed stream 124 into at least a CO-rich stream 128 and an H2-rich stream 130, but can also include minor amounts of one or more residual or tail gas streams of mixed H2 and CO which can be used as fuel or exported (not shown). The CO-rich stream 128 and H2-rich stream 130 can be supplied to alternate processes, such as, for example, acetic acid synthesis units or ammonia synthesis units, respectively, which are further discussed below.

Figure 2:
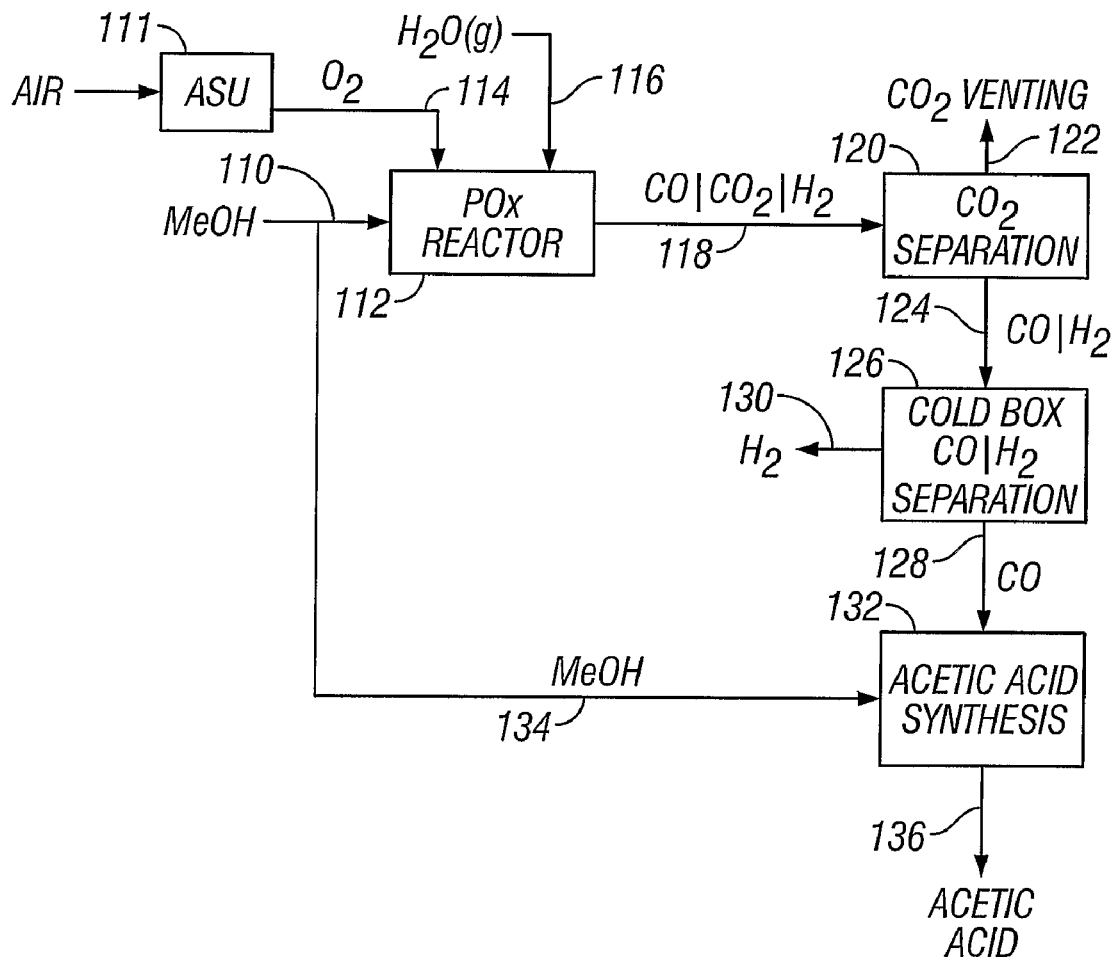
FIG. 2 is a simplified overall block flow diagram for the plant of FIG. 1, wherein an acetic acid reactor has been added for the synthesis of acetic acid.

As shown in FIG. 2, CO-rich stream 128 can be supplied to an acetic acid synthesis unit 132 where it is combined with a methanol stream 134, which can be obtained from the same feedstock that supplies the POX reactor 112. The acetic acid synthesis unit 132 can employ manufacturing equipment and methodology well known and/or commercially available to those skilled in the art to form acetic acid 136 from CO via stream 128 and methanol via stream 134, such as, for example, from one or more of the acetic acid manufacturing patents mentioned above. For example, a conventional BP/Monsanto process can be employed, or an improved BP/Monsanto process employing BP-Cativa technology (iridium catalyst), Celanese low water technology (rhodium-lithium acetate catalyst), Millennium low water technology (rhodium-phosphorus oxide catalyst) and/or dual process methanol carbonylation-methyl formate isomerization. The reaction generally comprises reacting methanol, methyl formate, or a combination thereof in the presence of a reaction mixture comprising carbon monoxide, water, a solvent and a catalyst system comprising at least one halogenated promoter and at least one compound of rhodium, iridium, or a combination thereof.

The reaction mixture for the acetic acid synthesis preferably has a water content of less than 20 weight percent, more preferably between approximately 14 and 15 weight percent. When the reaction comprises low water carbonylation, the water content in the reaction mixture is preferably from about 2 to about 8 weight percent. When the reaction comprises methyl formate isomerization or a combination of isomerization and methanol carbonylation, the reaction mixture preferably contains a nonzero quantity of water up to 2 weight percent.

Figure 3:
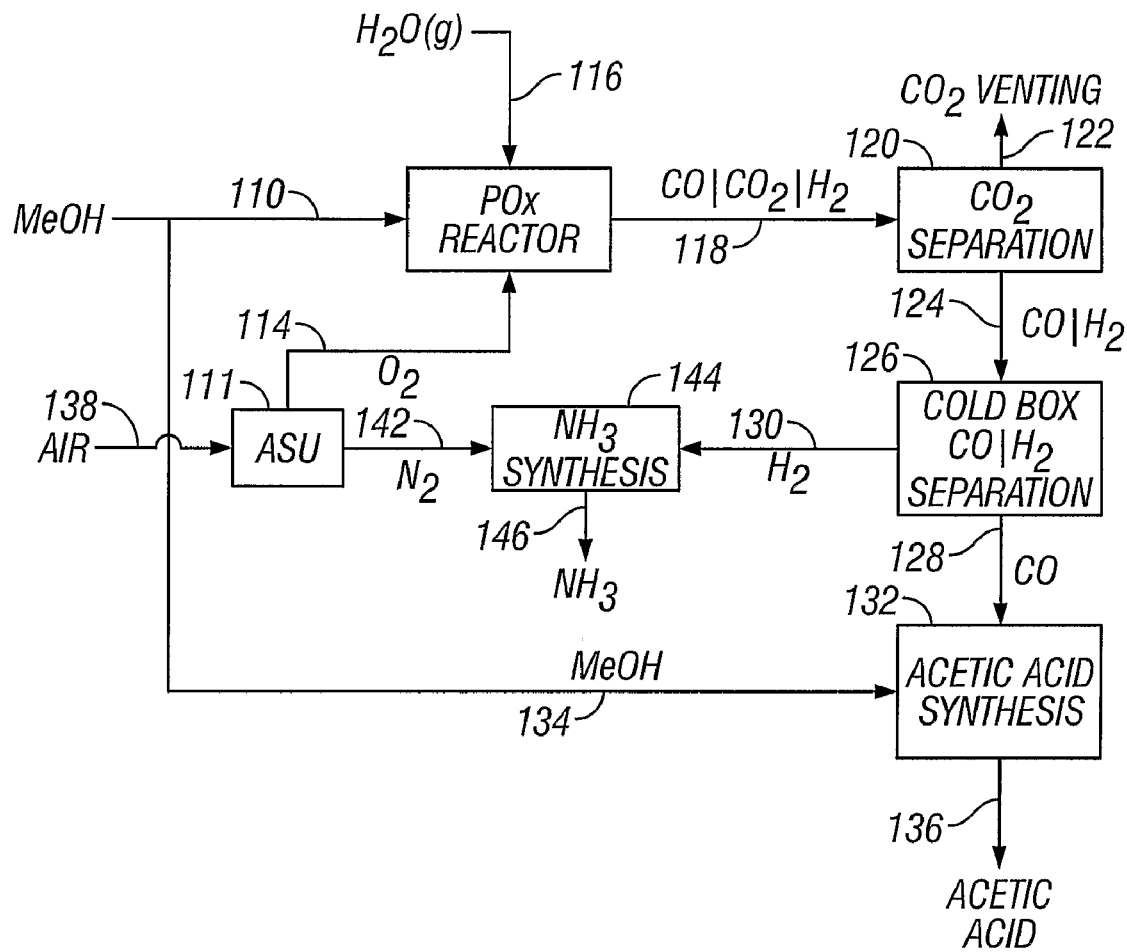
FIG. 3 is a simplified overall block flow diagram for the plant of FIG. 2, wherein an ammonia synthesis reactor has been added for the synthesis of ammonia.

As shown in FIG. 3, the process can optionally include an ammonia synthesis unit 144, designed to take advantage of the H2 from the syngas stream 118 and nitrogen from the ASU 111. All or a portion of hydrogen stream 130 from the CO/H2 separation unit 126 is reacted with an N2 stream 142 from the air separation unit to form ammonia collected in stream 146. Ammonia output from the synthesis unit 144 can be increased by increasing hydrogen feed, or by adding a second ammonia synthesis unit (not shown).

Figure 4:
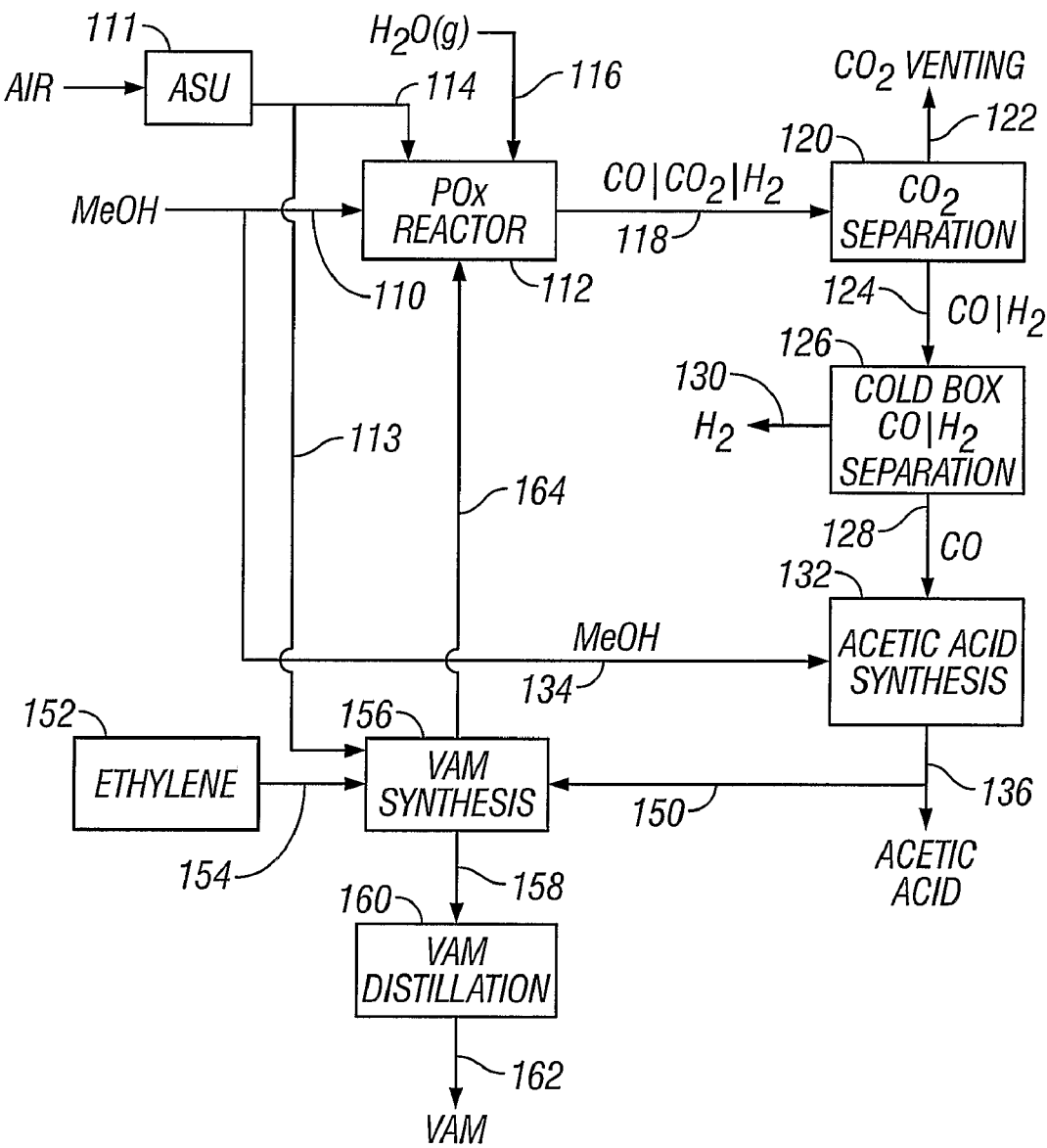
FIG. 4 is a simplified overall block diagram for the plant of FIG. 2, wherein a vinyl acetate monomer reactor has been added for the synthesis of vinyl acetate monomer.

As shown in FIG. 4, the process can optionally include a vinyl acetate monomer (VAM) synthesis unit 156. A portion of the acetic acid from line 136 can be fed via line 150 to an the VAM synthesis unit 156 where it can be reacted with ethylene 152 via line 154 and at least a portion of the oxygen 113 from air separation unit 111. A liquid product stream 158 is processed via conventional VAM distillation unit 160 to produce essentially pure (commercial specification) VAM via line 162. Carbon dioxide produced as a byproduct of the VAM synthesis can be separated from the reactor effluent gases via a conventional CO2 removal system (not shown) and recycled to the POX reactor 112 via line 164.

VAM production can be mainly achieved by the acetoxylation of ethylene according to the reaction:

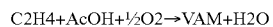

The main by-product CO2 is formed by the reaction

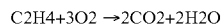

Selectivity for the process yields approximately 7-8% CO2 by mass. Typically, a VAM plant producing approximately 100,000 metric tons per year (MTY) of VAM requires approximately 35,000 MTY of ethylene and produces between 5,000 and 10,000 MTY of CO2.

Figure 5:
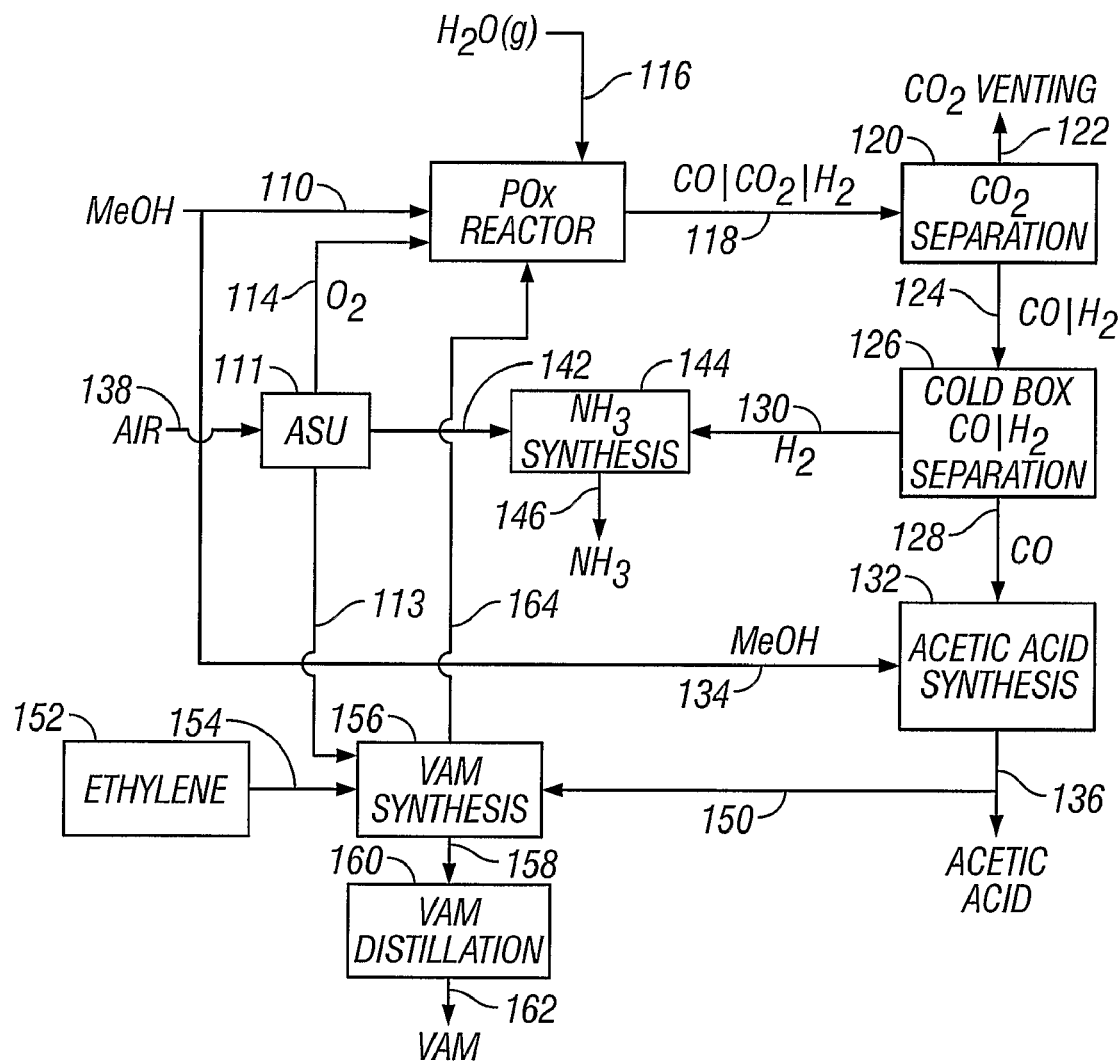
FIG. 5 is a simplified overall block diagram for the plant of FIG. 3, wherein a vinyl acetate monomer reactor has been added for the synthesis of vinyl acetate monomer.

As shown in FIG. 5, a vinyl acetate synthesis unit 156 can be added to the existing acetic acid synthesis unit 132 and ammonia synthesis unit 144 for optimal usage of the syngas stream. The VAM synthesis unit 156 can be supplied with a portion of the acetic acid product stream 136 via line 150 for the synthesis of the monomer. Crude VAM exits the VAM synthesis unit 156 via line 158 and enters a distillation unit 160 to produce a product stream 162. Carbon dioxide produced as a byproduct of the VAM synthesis can be separated from the reactor effluent gases via a conventional CO2 removal system (not shown) and recycled to the POX reactor 112 via line 164.

Figure 6:
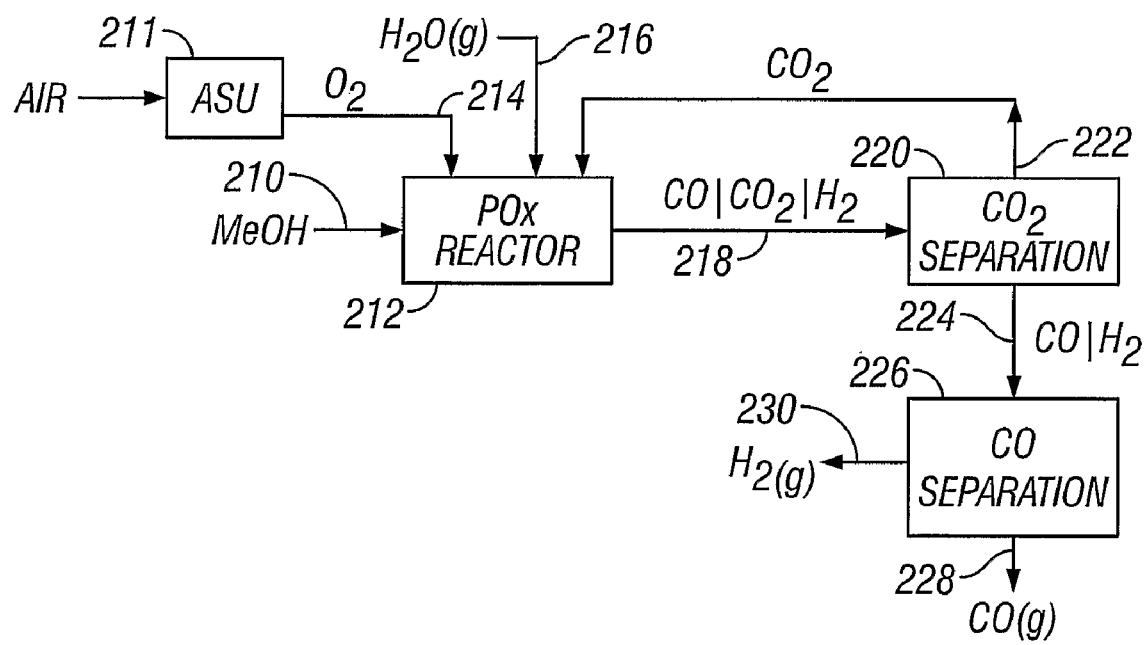
FIG. 6 is a simplified overall block flow diagram for an alternate embodiment of the present invention for the production of hydrogen and carbon monoxide from methanol wherein carbon dioxide is separated and recycled to the reactor.

As shown in FIG. 6, all or a portion of the carbon dioxide 222 produced and separated from the syngas effluent 218 and recycled to the POX reactor 212. A methanol stream 210 is supplied to the partial oxidation (POX) reactor 212 of an existing methanol synthesis plant, where it is combined with oxygen 214 and carbon dioxide 222. The methanol stream 210 is preferably a pre-existing methanol feedstock which has been previously purified by distillation or another conventional process (not shown). The oxygen 214 is obtained from pre-existing air separation unit (ASU) 211, which is fed with air compressed. Carbon dioxide 222 can be produced in the reformation of the methanol 210 and can be recycled to the reactor 212 feed.

POX reactor 212 can produce a syngas effluent 218 consisting of H2, CO and CO2. The effluent 218 is generally cleaner than syngas produced from a natural gas feed as much of the impurities are removed during synthesis of the feedstock. Effluent 218, after cooling, can be fed to CO2 separation unit 220 which produces a CO2-rich stream 222 and a mixed CO/H2 stream 224 essentially free of CO2. The CO2-rich stream 222 can be recycled to the POX reactor 212 and the mixed CO/H2 stream 224 is supplied to separation unit 226. Recycle of the CO2-rich stream to the POX reactor can increase CO production between approximately 5-10% and decrease hydrogen production between approximately 3-8%.

When the CO2 is recycled to the POX reactor, for a given production rate, the methanol feed requirement is thus reduced.

Separation unit 226 preferably includes molecular sieves and a conventional cold box. The separation unit 226 splits the stream 224 into at least a CO-rich stream 228 and an H2-rich stream 230, but can also include minor amounts of one or more residual or tail gas streams of mixed H2 and CO which can be used as fuel, recycled to the reactor, or exported (not shown).

Figure 7:
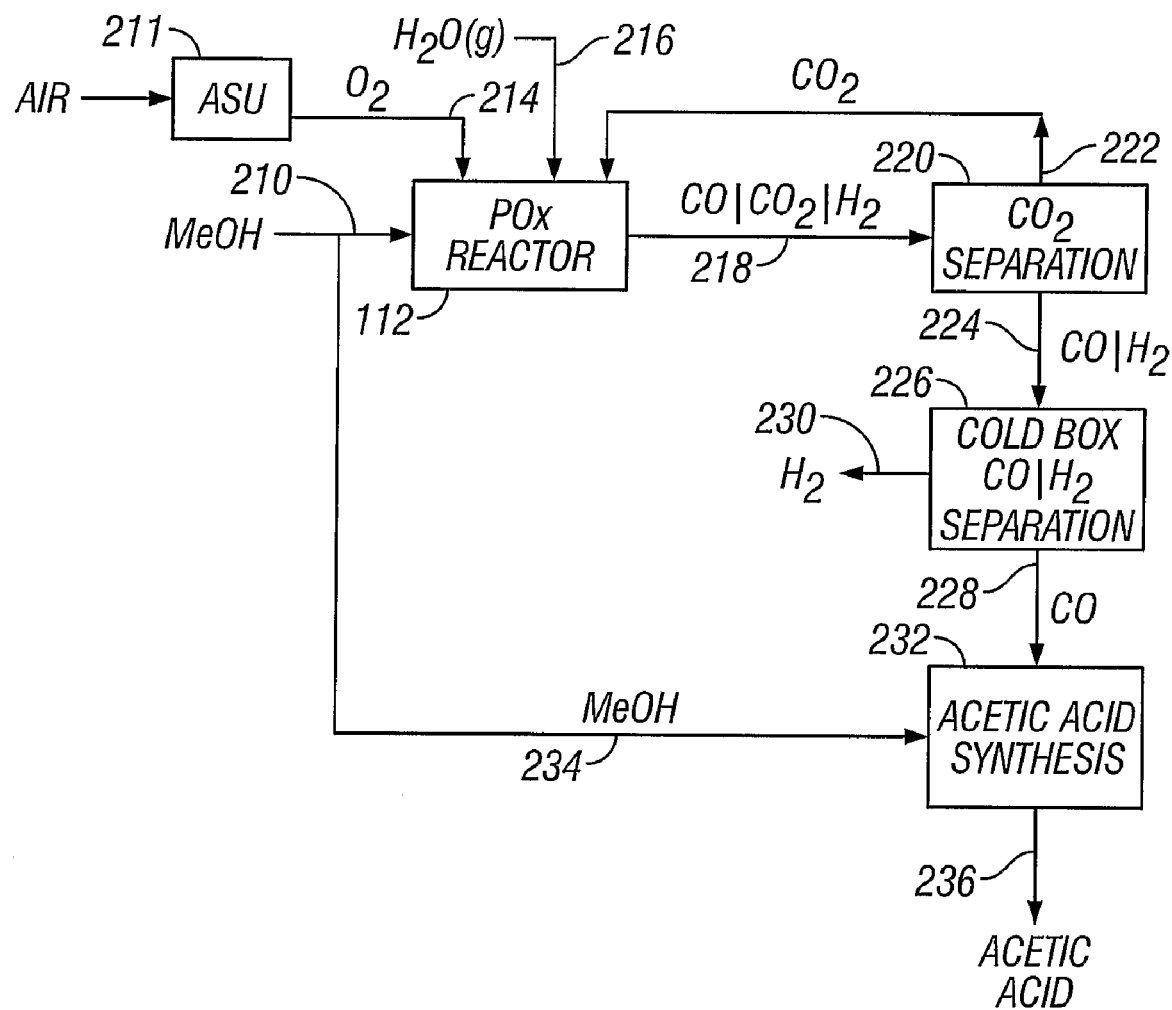
FIG. 7 is a simplified overall block flow diagram for the plant of FIG. 6, wherein an acetic acid reactor has been added for the synthesis of acetic acid.
Figure 8:
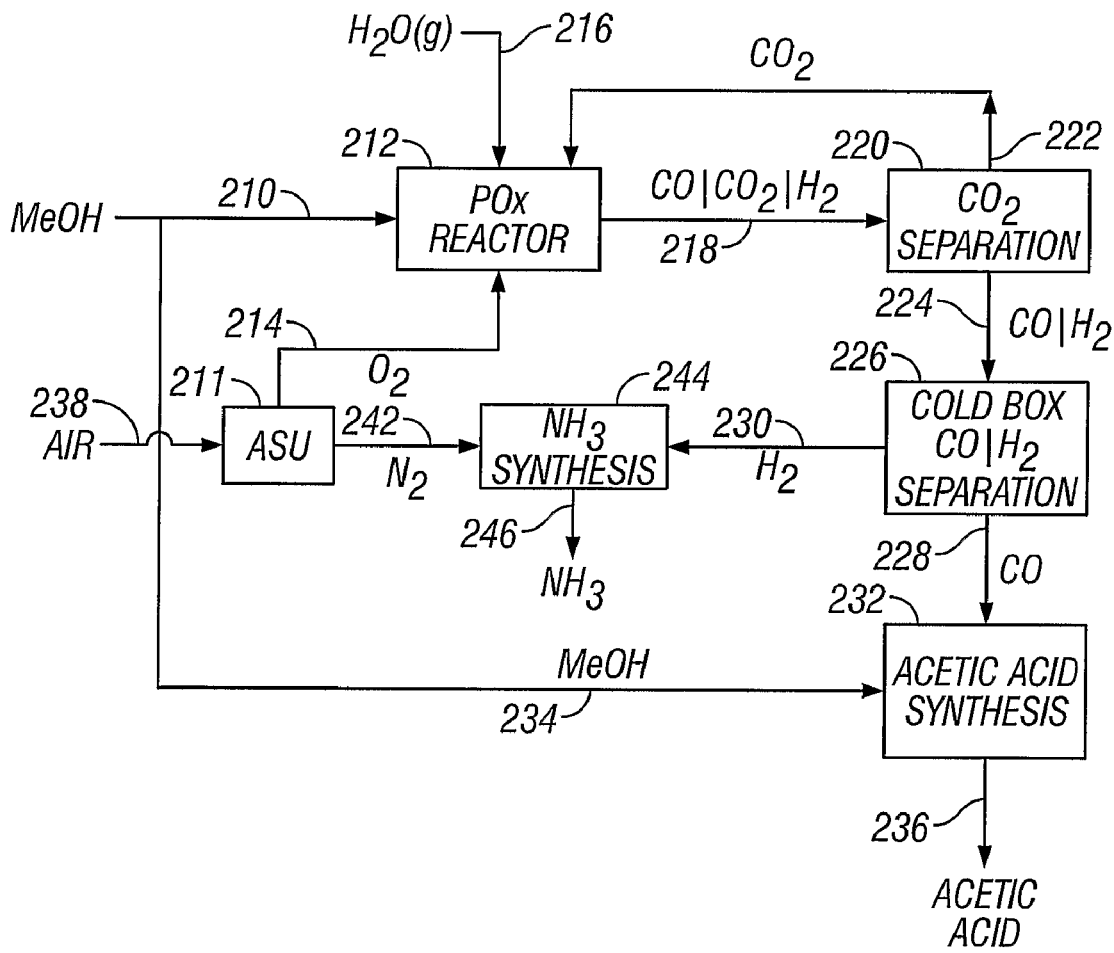
FIG. 8 is a simplified overall block flow diagram for the plant of FIG. 7, wherein an ammonia reactor has been added for the synthesis of ammonia.

As shown in FIG. 7, CO-rich stream 228 can be combined with a stoichiometric amount of the methanol feedstock 234 to yield acetic acid 236, by a synthetic process which has been described above. As shown in FIG. 8, the H2-rich stream 230 can be reacted with nitrogen 242 from ASU 240 in an ammonia synthesis unit 244 to yield ammonia product 246. Alternatively, all or a portion of the H2-rich stream can be supplied as fuel or exported to an alternate process (not shown).

Figure 9:
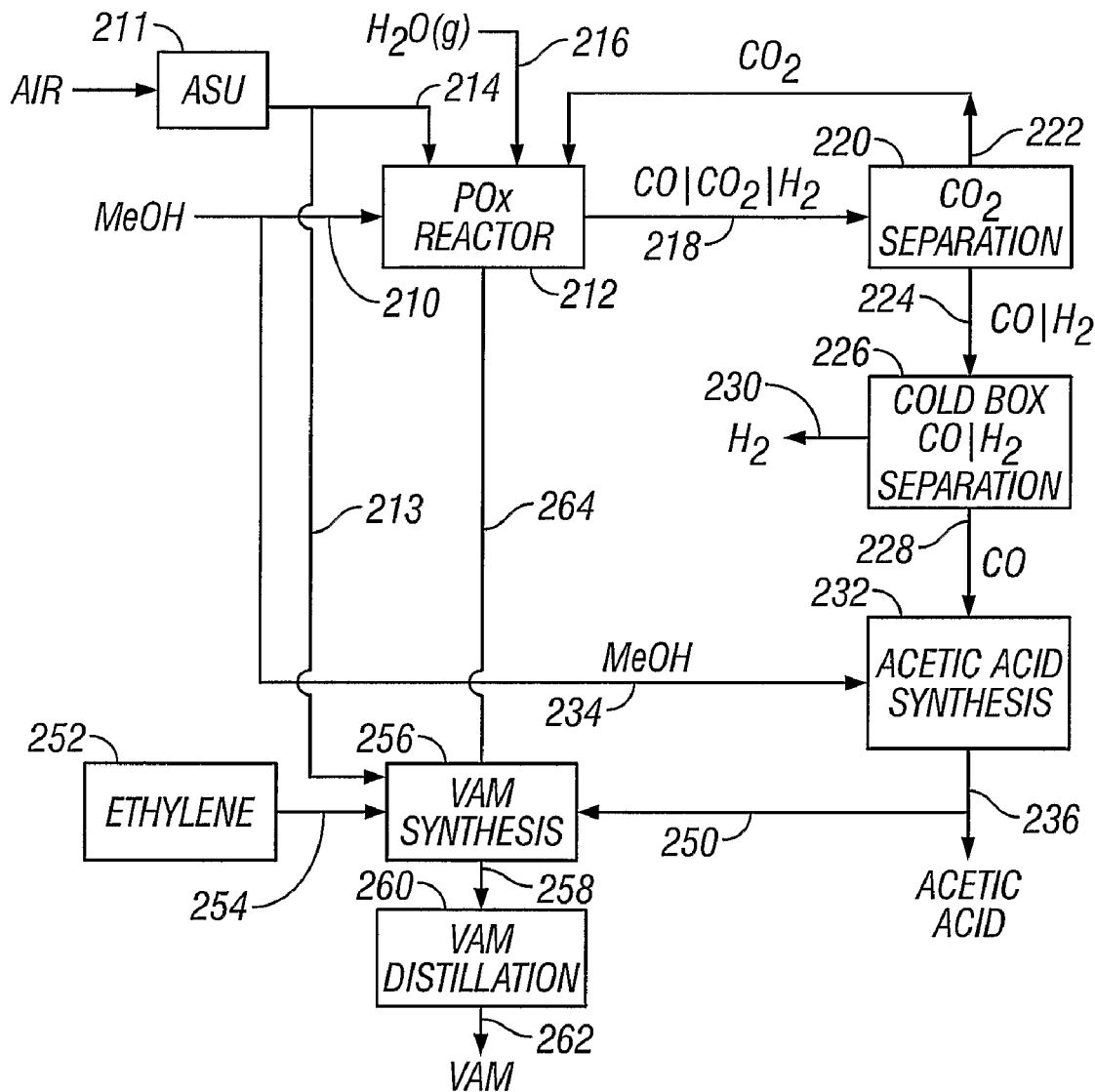
FIG. 9 is a simplified overall block diagram for the plant of FIG. 7, wherein a vinyl acetate monomer reactor has been added for the synthesis of vinyl acetate monomer.

As shown in FIG. 9, the process can optionally include a vinyl acetate monomer (VAM) synthesis unit 256. A portion of the acetic acid from line 236 can be fed via line 250 to an the VAM synthesis unit 256 where it is reacted with ethylene 252 via line 254 and at least a portion of the oxygen 213 from air separation unit 211. A liquid product stream 258 can be processed via conventional VAM distillation unit 260 to produce essentially pure (commercial specification) VAM via line 262. Carbon dioxide produced as a byproduct of the VAM synthesis can be separated from the reactor effluent gases via a conventional CO2 removal system (not shown) and recycled to the POX reactor 212 via line 264.

Figure 10:
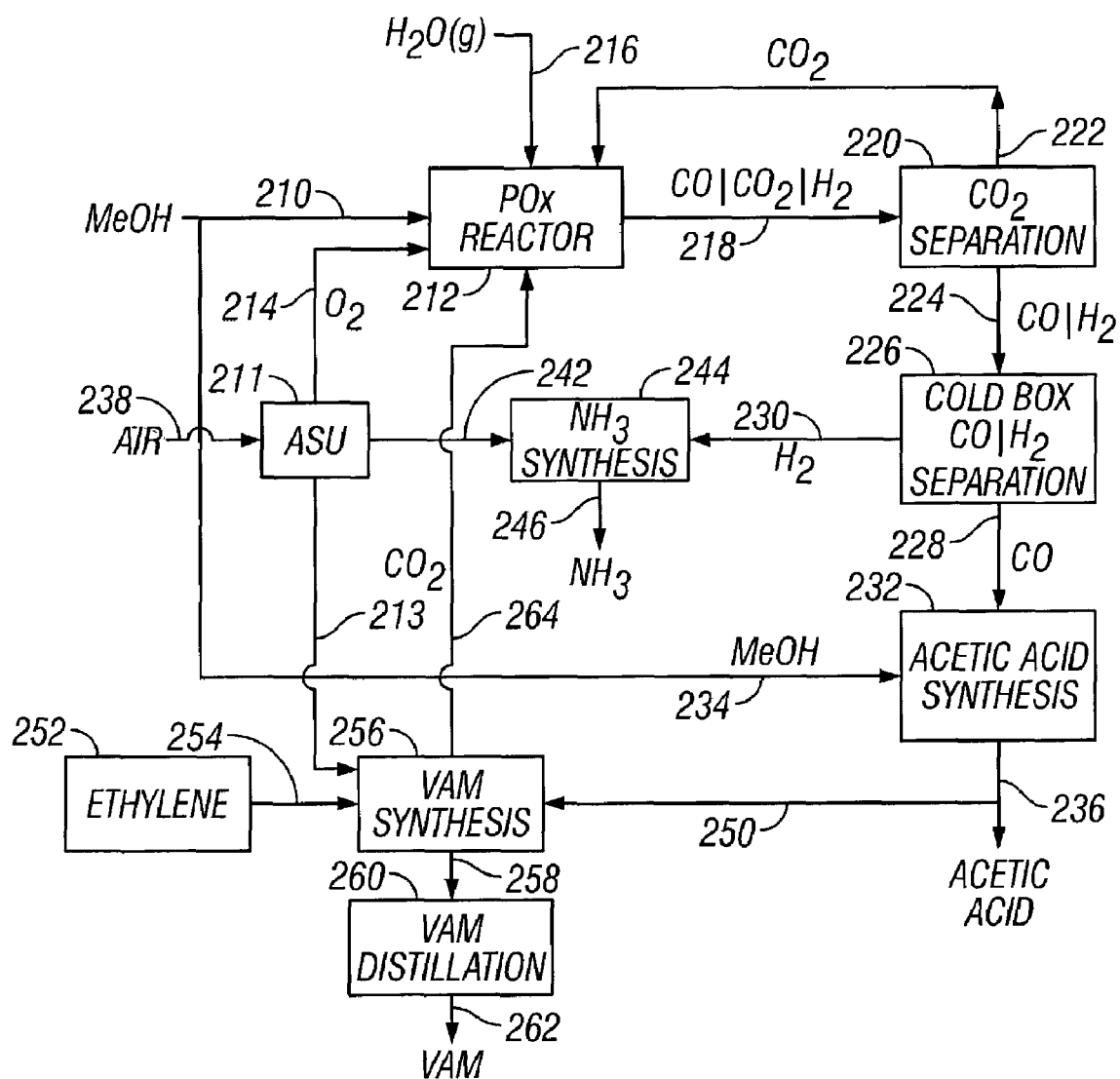
FIG. 10 is a simplified overall block diagram for the plant of FIG. 8, wherein a vinyl acetate monomer reactor has been added for the synthesis of vinyl acetate monomer.

As shown in FIG. 10, a vinyl acetate synthesis unit 256 can be added to the existing acetic acid synthesis unit 232 and ammonia synthesis unit 244 for optimal usage of the syngas stream. VAM synthesis unit 256 can be supplied with a portion of the acetic acid product stream 236 via line 250, ethylene 252 via line 254, and oxygen from the ASU 211 via line 213. Crude VAM exits the VAM synthesis unit 256 via line 258 and enters a distillation unit 260 to produce a product stream 262. Carbon dioxide produced as a byproduct of the VAM synthesis can be separated from the reactor effluent gases via a conventional CO2 removal system (not shown) and recycled to the POX reactor 212 via line 264.

Utilities (not shown), which typically include the steam system, cooling water, compressed air and the like, can be supplied from a pre-existing methanol plant and can be used to supply an associated processes, such as, for example, acetic acid and ammonia synthesis units, as well. Steam generated by waste heat recovery from the acetic acid synthesis unit 132 and/or any other associated integrated unit, can be used to drive or supply steam to water pumps (not shown), ASU compressor 111, POX reactor 112, CO2 removal unit 120, and the like.

The partial oxidation reactors can be unpacked, free-flow, non-catalytic gas generators to which preheated hydrocarbon and oxygen are supplied. Optionally, a temperature moderator can be supplied to the reactor as well. The partial oxidation reactor effluent is then quenched or cooled, and optionally cleaned to remove soot and other particulate impurities, and can be further processed or separated for additional downstream uses. When hydrogen gas is the desired end product, such as, for example, for ammonia synthesis reactors, high and low temperature shift converters can be employed to convert CO and steam to hydrogen and CO2. Where carbon monoxide is the desired end product, such as, for example, for acetic acid synthesis reactors, any CO2 can be removed and recycled to the reactor to increase CO production, or reverse shift reactors can be employed to convert CO2 and H2 to CO and H2O.

When the partial oxidation reactor is from a pre-existing methanol plant, the burner can be adjusted for operation for use with a methanol feedstock. The partial oxidation reactor temperature can be maintained from 1100°-2000° C. (2000°-3600° F.), preferably from 1300°-1500° C. (2400°-2700° F.). The reactor pressure can be maintained at between 2 and 6 MPa, preferably approximately 4 MPa.

The production of syngas from liquid and solid carbon materials can often result in the presence of many unwanted impurities, such as for example, CO2, SO2, COS, CH4, Ar, N2, H2O and NH3. Typically, when natural gas is used as the feedstock for the production of syngas, a desulfurizing/saturation unit with a catalyst bed, such as, for example, nickel/molybdenum catalyst can be used to remove sulfur from feed prior to supplying to the reactor. Because the natural gas used in the synthesis of the methanol has already desulfurized and the methanol product has already been purified by distillation or another conventional purification process, many of the undesired impurities normally present from synthesis with natural gas are effectively eliminated from the syngas product.

The effluent from the partial oxidation has a molar ratio of H2-CO2 to CO+CO2 (referred to in the present specification as the "R ratio" (H2-CO2)/(CO+CO2)), which can be optimized for the production of CO. Generally, for the production of methanol, an R ratio of approximately 2.0 is desired. For the synthesis of syngas high in CO, the H2 to CO ratio can range from 1.5 to 3, and preferably between 1.5 and 2.

Suitable temperature moderators, to control the reaction conditions, can be added to the reaction zone and can include H2O, CO2, and N2 from the air separation unit, flue gas, cooled and recycled effluent gas, and mixtures thereof. The need for a temperature moderator is generally driven by the carbon:hydrogen ratio of the hydrocarbon feed and the presence of free oxygen. Preferably, the temperature moderator can include a portion of CO2 cooled and separated from the partial oxidation reactor effluent and recycled back to the reactor feed. When steam is used as the temperature moderator, control of the flow rate can limit or prevent the production of soot in the reactor.

The CO2 removal unit separates the effluent stream into a CO2-rich and a CO2-lean stream using conventional CO2 separation equipment and methodology, such as, for example, absorption-stripping with a solvent such as water, methanol, generally aqueous alkanolamines such as ethanolamine, diethanolamine, methyldiethanolamine and the like, aqueous alkali carbonates such as sodium and potassium carbonates, and the like. Such CO2 absorption-stripping processes are commercially available under the trade designations Girbotol, Sulfinol, Rectisol, Purisol, Fluor, BASF (aMDEA) and the like.

The CO2-lean stream contains primarily CO and hydrogen and can be separated in a CO separation unit into CO-rich and hydrogen-rich streams. The separation unit can comprise any equipment and/or methodologies known in the art for separating the CO and hydrogen mixture into relatively pure CO and hydrogen streams, such as, for example, semi-permeable membranes, cryogenic fractionation, or the like. Cryogenic fractional distillation is preferred, and can include simple partial condensation without any columns, optionally with a pressure swing absorption (PSA) unit and a hydrogen recycle compressor, or methane wash. Partial condensation with columns is typically sufficient for obtaining CO and hydrogen of sufficient purity for acetic acid and ammonia production, respectively, keeping the equipment and operating costs to a minimum. The PSA unit and hydrogen recycle compressor can be added for increasing the hydrogen purity and CO production rates if desired. For the manufacture of acetic acid, the CO stream preferably contains less than 1000 ppm hydrogen and less than 2 mole percent nitrogen plus methane. For ammonia production, the hydrogen stream which is sent to a nitrogen wash unit (not shown) preferably contains at least 80 mol % hydrogen, and more preferably contains at least 95 mol % hydrogen.

EXAMPLE 1

A methanol feedstock stream is supplied to a partial oxidation reactor for the recovery of hydrogen and carbon monoxide. The methanol stream is supplied at a rate of 1438 kmoles/hour, where it is combined with 719 kmoles/hour of oxygen and 884 kmoles/hour of steam. The partial oxidation reactor is operated at approximately 1300° C. (2372° F.) and 4 MPa, producing a syngas effluent stream. Carbon dioxide can be removed from the syngas stream, producing a carbon dioxide-rich stream and a carbon dioxide-lean stream of carbon monoxide and hydrogen. The carbon dioxide-rich stream can be vented or collected. The carbon dioxide-lean stream can be supplied to a cold box where the component hydrogen and carbon monoxide are separated, yielding 1045 kmoles/hour of carbon monoxide and 1812 kmoles/hour of hydrogen.

EXAMPLE 2

A methanol feedstock stream is fed to a partial oxidation reactor for recovery of hydrogen and carbon monoxide. The methanol stream is supplied at a rate of 1438 kmoles/hour, where it is combined with 719 kmoles/hour of oxygen, 350 kmoles/hour of steam, and 296 kmoles/hour of carbon dioxide recycled from the reactor effluent. The partial oxidation reactor operates at approximately 1400° C. (2552° F.) and 4 MPa, producing a syngas effluent stream. Carbon dioxide is removed from the syngas stream by known means, producing a carbon dioxide-rich stream and a carbon dioxide-lean stream of carbon monoxide and hydrogen. The carbon dioxide-rich stream is recycled to the partial oxidation reactor at a rate of 296 kmoles/hour. The carbon dioxide-lean stream is supplied to a cold box where the components are separated, yielding 1045 kmoles/hour of carbon monoxide and 1812 kmoles/hour of hydrogen.

EXAMPLE 3

The production of acetic acid from a plant having the operating conditions of Example 1. A stoichiometric amount of methanol (1045 kmoles/hour) is added to the carbon monoxide-rich stream (1045 kmoles/hour) in an acetic acid synthesis unit to produce approximately 1045 kmoles/hour of acetic acid.

EXAMPLE 4

The production of acetic acid from a plant having the operating conditions of Example 2. A stoichiometric amount of methanol (1134 kmoles/hour) is added to the carbon monoxide-rich stream (1134 kmoles/hour) in an acetic acid synthesis unit to produce approximately 1134 kmoles/hour of acetic acid.

The invention is described above in reference to specific examples and embodiments. The metes and bounds of the invention are not to be limited by the foregoing disclosure, which is illustrative only, but should be determined in accordance with the full scope and spirit of the appended claims. Various modifications will be apparent to those skilled in the art in view of the description and examples. It is intended that all such variations within the scope and spirit of the appended claims be embraced thereby.

The invention claimed is:

1. A method for preparing a hydrogen-rich stream and a carbon monoxide-rich stream, comprising:
   reacting a methanol feed stream and oxygen, and optionally a temperature moderator, in a partial oxidation reactor to produce a syngas stream, wherein the partial oxidation reactor is catalyst-free and operated at a temperature between 1100° and 2000° C.;
   separating the syngas stream into a carbon dioxide rich stream and a mixed stream containing hydrogen/carbon monoxide; and
   separating the mixed stream into a hydrogen-rich stream and a carbon monoxide-rich stream.

2. The method of claim 1, further comprising vaporizing the methanol feed stream supplied to the partial oxidation reactor.

3. The method of claim 1, wherein the temperature moderator is selected from steam, carbon dioxide, nitrogen, cooled and recycled effluent, or mixtures thereof.

4. The method of claim 1, wherein the temperature moderator is a carbon dioxide-rich stream recycled from the reactor effluent.

5. The method of claim 1, wherein the partial oxidation reactor is operated at a temperature between 1300° and 1500° C.

6. The method of claim 1, further comprising reacting a portion of the methanol feed stream with the carbon monoxide rich stream to produce acetic acid.

7. The method of claim 1, further comprising:
   providing a nitrogen stream from an air separation unit, and
   supplying the nitrogen stream and the hydrogen-rich stream to an ammonia synthesis unit to produce ammonia.

8. The method of claim 6, further comprising:
   providing an ethylene stream;
   supplying the ethylene stream, oxygen, and acetic acid to a vinyl acetate monomer synthesis unit to produce vinyl acetate monomer.

9. The method of claim 8, wherein the oxygen supplied to the partial oxidation reactor and to the vinyl acetate monomer synthesis unit is provided by a single air separation unit.

10. A method for converting an original methanol plant to a converted plant for the synthesis of acetic acid, the method comprising the steps of:
    providing the original methanol plant having
      at least one partial oxidation reactor for converting a hydrocarbon to a syngas stream containing hydrogen, carbon monoxide and carbon dioxide; and
      a methanol synthesis loop for converting hydrogen and carbon monoxide from the syngas stream to methanol;
    providing for supplying at least a portion of a methanol feedstock stream, oxygen from an air separation unit and optionally, a temperature moderator, to the at least one partial oxidation reactor, wherein the partial oxidation reactor is catalyst-free and operated at a temperature between 1100° and 2000° C.;
    installing a first separation unit for separating a carbon dioxide-rich stream and a mixed hydrogen/carbon monoxide stream from the syngas effluent;

installing a second separation unit for separating a hydrogen-rich stream and a carbon monoxide rich stream from the mixed stream;

installing an acetic acid synthesis unit;

providing for supplying the carbon monoxide-rich stream from the second separation unit and a portion of the methanol feedstock stream to the acetic acid synthesis unit; and installing isolation valves for isolating the methanol synthesis loop from the remainder of the converted plant.

11. The method of claim 10, wherein the methanol feedstock is vaporized for supply to the partial oxidation reactor.

12. The method of claim 10, further comprising:

installing an ammonia synthesis unit for reacting a hydrogen-rich stream and nitrogen to form ammonia;

providing for supplying at least a portion of the hydrogen-rich stream from the separation unit to the ammonia synthesis unit; and providing a nitrogen stream from the air separation unit to the ammonia synthesis unit.

13. The method of claim 10, further comprising:

installing a vinyl acetate monomer synthesis unit for reacting ethylene, oxygen, and acetic acid to form vinyl acetate monomer;

providing for supplying at least a portion of the oxygen from an air separation unit to the vinyl acetate monomer synthesis unit; and producing a carbon dioxide-rich stream in the vinyl acetate monomer synthesis unit.

14. The method of claim 13, further comprising recycling the carbon dioxide-rich stream to the partial oxidation reactor.

15. The method of claim 11, further comprising recycling at least a portion of the carbon dioxide-rich stream to the partial oxidation reactor as a temperature moderator.

16. The method of claim 11, wherein the temperature moderator is steam.

17. The method of claim 1, further comprising reacting the carbon monoxide-rich stream with methanol in an acetic acid synthesis unit to produce acetic acid and converting an original methanol plant to a converted plant for the synthesis of the acetic acid, wherein the original methanol plant comprises the partial oxidation reactor and a methanol synthesis loop associated therewith, and the conversion of the plant comprises the steps of:

installing the acetic acid synthesis unit;

installing isolation valves for isolating the methanol synthesis loop from the remainder of the converted plant;

importing a methanol feedstock stream;

providing for supplying (1) the vaporized methanol feed stream from a first portion of the methanol feedstock stream, (2) the oxygen, and (3) the optional temperature moderator, to the partial oxidation reactor to produce the syngas stream;

installing a first separation unit for the separation of the carbon dioxide-rich stream and the mixed hydrogen/carbon monoxide stream from the syngas stream;

installing a second separation unit for the separation of the hydrogen-rich stream and the carbon monoxide rich stream from the mixed stream; and providing for supplying the carbon monoxide-rich stream from the second separation unit and a second portion of the methanol feedstock stream to the acetic acid synthesis unit.

18. The method of claim 1, wherein the methanol feed stream supplied to the partial oxidation reactor is a purified commercial methanol product.

* * * * *